(12) United States Patent
Lian et al.

(10) Patent No.: US 12,146,885 B2
(45) Date of Patent: *Nov. 19, 2024

(54) BIOMARKERS FOR DIAGNOSING IMPLANT RELATED RISK OF IMPLANT REVISION DUE TO ASEPTIC LOOSENING

(71) Applicant: LYFSTONE B.V., Abcoude (NO)

(72) Inventors: Stein Lian, Kvaloya (NO); Jarle Mikalsen, Tromsdalen (NO); Eric Bendiksen, Krokelvdalen (NO); Anders Einung Hansen, Tromso (NO)

(73) Assignee: Lyfstone B.V., Abcoude (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,622

(22) Filed: Dec. 16, 2022

(65) Prior Publication Data

US 2023/0160910 A1    May 25, 2023

Related U.S. Application Data

(63) Continuation of application No. 17/812,537, filed on Jul. 14, 2022, which is a continuation of application No. 16/483,784, filed as application No. PCT/EP2018/053044 on Feb. 7, 2018, now Pat. No. 11,402,389.

(30) Foreign Application Priority Data

Feb. 7, 2017  (NO) .................................. 20170185

(51) Int. Cl.
  *G01N 33/53* (2006.01)
  *G01N 33/68* (2006.01)
(52) U.S. Cl.
  CPC . *G01N 33/6887* (2013.01); *G01N 2333/4727* (2013.01); *G01N 2800/108* (2013.01); *G01N 2800/52* (2013.01); *G01N 2800/56* (2013.01)
(58) Field of Classification Search
  None
  See application file for complete search history.

(56) References Cited

U.S. PATENT DOCUMENTS

| | | | |
|---|---|---|---|
| 5,776,348 | A | 7/1998 | Selengut et al. |
| 11,402,389 | B2 * | 8/2022 | Lian .................. G01N 33/6887 |
| 2005/0288211 | A1 | 12/2005 | Tessier et al. |
| 2006/0134705 | A1 | 6/2006 | Sundrehagen |
| 2015/0110811 | A1 | 4/2015 | De Min et al. |

FOREIGN PATENT DOCUMENTS

| | | |
|---|---|---|
| EP | 0585201 | 3/1994 |
| RU | 2305285 | 8/2007 |
| WO | WO 2006/047820 | 5/2006 |
| WO | WO 2008/114022 | 9/2008 |

OTHER PUBLICATIONS

Berntzen et al., "The Major Leukocyte Protein L 1 as an Indicator of Inflammatory Joint Disease", Sc and J Rheumatology, Suppl. vol. 76, 1988, pp. 251-256.
Dapunt et al., "Neutrophil-derived MRP-14 is up-regulated in infectious osteomyelitis and stimulates osteoclast generation", Journal of Leukocyte Biology, vol. 98, Oct. 2015, p. 575-582.
Dapunt et al., "On the inflammatory response in metal-on-metal implants", Journal of Translational Medicine, vol. 12, No. 1, 2014, p. 74.
Dapunt et al., "Osteoclast generation and cytokine profile at prosthetic Interfaces: a study on tissue of patients with aseptic loosening or implant-associated infections", European Journal ofInflammation, vol. 12, No. 1, 2014, pp. 147-159.
International Search Report issued Jul. 26, 2018 in International (PCT) Application No. PCT/EP2018/053044.
Kessel et al., "Phagocyte-derived S 100 proteins in auto inflanunation: Putative role in pathogenesis and usefulness as biomarkers", Clinical Immunology, vol. 147, 2013, pp. 229-241.
Klingberg et al., Calprotectin in ankylosing spondylitis—frequently elevated in feces, but normal in serum, Scandinavian Journal of Gastroenterology, 2012; 47: pp. 435-444. (Year: 2012).
Nordal et al., "Calprotectin (SIOOA8/A9) has the strongest association with ultrasound-detected synovitis and predicts response to biologic treatment: results from a longitudinal study of patients with established rheumatoid arthritis", Arthritis Research & Therapy, vol. 19, No. 3, 2017, pp. 1-10.
Office Action issued in AU application No. 2018217872, dated Nov. 30, 2020.
Office Action issued in corresponding CN application No. 201880022814.1, dated Apr. 15, 2022.
Office Action issued in EP application No. 18707053.6, dated Jun. 25, 2021.
Office Action issued in EP application No. 18708053.6, dated Jul. 27, 2020.
Office Action issued in EP application No. 18708053.6, dated Nov. 27, 2020.
Office Action issued in RU application No. 2019126238/04, dated May 28, 2021.
Response to Office Action issued in EP application No. 18708053.6, filed Sep. 30, 2020.
Response to Office Action issued in EP application No. 18708053.6, filed Mar. 25, 2021.
Schelbergen et al., "Alarmins SIO0A8/SIO0A9 aggravate osteophyte formation in experimental osteoarthritis and predictosteophyte progression in early human symptomatic osteoarthritis", Ann Rheum Dis vol. 75, 2016, pp. 218-225.

(Continued)

*Primary Examiner* — Gary Counts
(74) *Attorney, Agent, or Firm* — Knobbe, Martens, Olson & Bear, LLP

(57) ABSTRACT

Implant related risk of revision not caused by an infection or metal on metal reaction can be addressed by the methods provided herein, including diagnosing implant related risk of revision, use of kits for such diagnostic purposes and compositions for use in the treatment of implant related risk of revision, in particular implant related risk of revision not caused by an infection or metal on metal reaction.

20 Claims, 3 Drawing Sheets

(56) References Cited

OTHER PUBLICATIONS

Sumner et al., "Are There Biological Markers for Wear or Corrosion? A Systematic Review", Clin. Orthop. Relat. Res., vol. 472, 2014, pp. 3728-3739.

Torzewski et al., Animal Models of C-Reactive Protein, Hindawl Publishing Corporation, Mediators of Inflammation, 2014, pp. 1-7. (Year: 2014).

Van Der Vekiens et al., Human and equine cardiovascular endocrinology: beware to compare, Cardiovascular Endocrinology 2013, vol. 2, No. 4, pp. 67-76. (Year: 2013).

* cited by examiner

Aseptic loosening

Dislocation

BIOMARKERS FOR DIAGNOSING IMPLANT RELATED RISK OF IMPLANT REVISION DUE TO ASEPTIC LOOSENING

CROSS-REFERENCE TO RELATED APPLICATIONS

This application is a continuation application of U.S. patent application Ser. No. 17/812,537, filed Jul. 14, 2022, which is a continuation application of U.S. patent application Ser. No. 16/483,784, filed Aug. 6, 2019, and issued as U.S. Pat. No. 11,402,389 on Aug. 2, 2022, which is a National Stage entry of PCT Application No. PCT/EP2018/053044, filed Feb. 7, 2018, which claims priority to Norwegian Patent Application No. 20170185 filed Feb. 7, 2017, each of which is hereby incorporated by reference in its entirety.

FIELD

The present invention relates generally to the field of implant related risk of revision, in particular implant related risk of revision not caused by an infection or metal on metal reaction. The present invention provides methods of diagnosing implant related risk of revision, use of kits for such diagnostic purposes and compositions for use in the treatment of implant related risk of revision, in particular implant related risk of revision not caused by an infection or metal on metal reaction.

BACKGROUND

Approximately 1.5 million total hip replacement (total hip arthroplasty—THA) operations are carried out world-wide annually. This is likely to increase to approximately 3 million worldwide per annum within the next decade. In addition, other types of implants and joint replacements, such as knee, shoulder, foot, ankle, hand, wrist, elbow, cranio-maxillofacial and dental, are also being used in increasing amounts.

Prostheses for THA often consist of two components. An artificial socket, or acetabular component (FIG. 3), is located in a prepared cavity in the acetabulum of the pelvis (FIGS. 2 and 3). This articulates with a femoral component comprising a femoral head attached to a femoral stem (FIG. 3), which is introduced into a prepared cavity in the medulla of the femur. Many variations of both components exist, and they may be retained with or without cements. The goals of THA are to increase mobility, improve hip joint function, and relieve pain. Yet despite its success as a surgical procedure, THA is still considered a treatment of last resort because it requires excision of the entire femoral head. It is this major alteration of the femur that often makes revision replacement difficult.

While the THA procedure has a prosthesis survival rate of 90% or more in the elderly (who usually do not outlive the implant), implant lifetimes are significantly shorter in younger, more active patients. As a result, younger patients face the prospect of multiple, difficult revisions in their lifetime. Typically, a hip prosthesis lasts for at least 15-20 years before needing to be replaced. The expected failure rate of prosthetic implants over the first 10 years is approximately 3-5% and the failure rate is increasing for the next 10 years. In Norway data from 2012 demonstrate that revisions constitute 8.5% of all hip prosthetic operations.

Osteolysis and subsequent aseptic joint loosening, both being categorized as a pathology initiation condition, are the most common reasons for joint revision. At an early stage, this condition is typically associated with micromovement at the implant-bone interface causing progressive destruction of bone. Initially, this condition is often painless and because of this symptomless interval the loss of bone stock may be massive before patients seek advice. By then, the conditions for a revision procedure may be unfavorable and the expected survival time for a new prosthesis is decreased. Further, if pathology initiation is diagnosed before progressing to a more acute pathology, the condition may favorable be treated by e.g. using anti-inflammatory drugs. If the treatment is successful, it may not be necessary to proceed further with a revision procedure.

Thus, there is a need for methods which allows diagnosing early stage implant loosening, i.e. pathology initiation, even in asymptomatic patients.

Further, there is also a need for cost effective methods which allows identifying patients that is at risk of revision; i.e. identifying those patients who is in the need of treatment.

Diagnostic and prognostic biomarkers have the potential to provide an early, accurate, and noninvasive diagnosis of these undesired outcomes as well as help design interventions to prevent some of these complications, especially aseptic loosening, dislocation of implant and osteolysis. A number of studies have been reported discussing the use of biomarkers to diagnose aseptic loosening.

Int. J. Clin. Exp. Pathol. 2016; 9 (2):1954-1960 suggests that osteoclast morphology and activity in the peripheral blood and expression levels of MCP-1 can be used for early diagnosis of aseptic loosening after total hip replacement.

Int. Orthop. 2013 June; 37 (6): 1025-1031 refers to a study indicating that there was a significant change in the plasma level of multiple biomarkers, including PICP, OPG, TNF-a, NTX, RANKL and IL-1β, in patients with prosthetic aseptic loosening.

J Arthroplasty. 2005 December; 20 (8):1049-54 demonstrates that both IL-6 and IL-8 are associated with aseptic loosening.

Even though biomarkers suitable for diagnosing implant loosening after total hip replacement already have been discussed in the prior art, there is still a need for further biomarkers, and in particular biomarkers that are easily detectable at an early stage of implant loosening even in asymptomatic patients.

SUMMARY

The present inventors have solved this need by having identified biomarkers, and in particular calprotectin, S100A8 and S100A9, which allow early stage diagnosis of implant loosening, even in asymptomatic patients.
Methods of the Invention The present invention provides in a first aspect a method of diagnosing implant related risk of revision, the method comprising the following steps: providing a biological sample from a subject with an implant; detecting a level of at least one polypeptide selected from the group consisting of calprotectin, S100A8 and S100A9 in the biological sample; wherein the biological sample is synovial fluid, preferably synovial fluid from the site of the implant.

In one embodiment according to the present invention, the at least one polypeptide is one polypeptide selected from the group consisting of calprotectin, S100A8 and S100A9. In another embodiment according to the present invention, the at least one polypeptide is two polypeptides each being selected from the group consisting of calprotectin, S100A8 and S100A9; the two polypeptides not being identical. In a further embodiment according to the present invention, the at least one polypeptide is three polypeptides each being selected from the group consisting of calprotectin, S100A8 and S100A9; the three polypeptides not being identical.

In one embodiment according to the present invention, a level <4 mg/l of the at least one polypeptide is indicative of a diagnosis of no implant related risk of revision, such as a stable implant.

In one embodiment according to the present invention, a level ≥4 mg/l of the at least one polypeptide is indicative of a diagnosis of implant related risk of revision.

In one embodiment according to the present invention, a subject diagnosed with implant related risk of revision is a subject suffering from either pathology initiation or acute pathology.

In one embodiment according to the present invention, a level in the range 1-50 mg/L, such as in the range 4-50 mg/L, 5-50 mg/L, 6-50 mg/L, 7-50 mg/L or 8-50 mg/L of the at least one polypeptide being indicative of implant related risk of revision and in particular pathology initiation.

In one embodiment according to the present invention, a level in the range 1-50 mg/L, such as in the range 5-50 mg/L, 10-50 mg/L, 20-50 mg/L, 30-50 mg/L, 1-45 mg/L, 1-40 mg/L, 1-35 mg/L, 1-30 mg/L or 1-25 mg/L of the at least one polypeptide being indicative of implant related risk of revision and in particular pathology initiation.

In one embodiment according to the present invention, pathology initiation is selected from the group consisting of aseptic loosening, dislocation of the implant, osteolysis and/or any combination thereof.

In one embodiment according to the present invention a level >50 mg/l, such as >55 mg/L, >60 mg/L, >70 mg/L, >80, >90 mg/L or >100 mg/L, of the at least one polypeptide is indicative of acute pathology.

In another embodiment according to the present invention a level >50 mg/L of the at least one polypeptide is a level of 51-1000 mg/L, 55-1000 mg/L, 60-1000 mg/L, 70-1000 mg/L, 80-1000 mg/L, 90-1000 mg/L, 100-1000 mg/L, 51-900 mg/L, 51-850 mg/L, 51-800 mg/L, 51-700 mg/L, 51-650 mg/L, 51-600 mg/L, 51-550 mg/L or 51-500 mg/L.

In one embodiment according to the present invention acute pathology is selected from the group consisting of implant-associated infection and metal-on-metal reaction, in particular implant-associated infection.

According to particular embodiments, implant-associated infection is selected from the group consisting of septic loosening, chronic joint infection, biofilm infection and/or any combination thereof.

In one embodiment according to the present invention wherein the method is for diagnosing pathology initiation.

According to particular embodiments, implant related risk of revision, in particular pathology initiation, is selected from the group consisting of inflammatory joint disease, osteoporosis, aseptic loosening, synovitis/synovial inflammation, wear and particle debris, misalignment of implant, fracture, ALVAL, stability of joint and/or implant including instability of one or both.

According to particular embodiments, the method is not for diagnosing acute pathology.

According to other particular embodiments, the method is for diagnosing implant related risk of revision that is not caused by implant-associated infection. Implant-associated infection preferably being selected from the group consisting of septic loosening, chronic joint infection, biofilm infection and/or any combination thereof.

According to particular embodiments, the method is for diagnosing implant related risk of revision that is not caused by metal-on-metal reaction.

In one embodiment according to the present invention, the method further comprises comprising a step of comparing the level of the at least one polypeptide in the biological sample with the level of the at least one polypeptide in a control sample. The control sample preferably being a synovial fluid sample from a subject not suffering from implant related risk of revision.

According to particular embodiments, the subject to be diagnosed fails to show any noticeable symptoms with which implant related risk of revision is associated.

According to particular embodiments, the subject to be diagnosed is an asymptomatic subject.

According to particular embodiments, the subject to be diagnosed does not have any symptoms of implant related risk of revision.

According to particular embodiments, the biological sample is synovial fluid collected at the site of the implant.

According to particular embodiments, the implant is a joint implant. According to particular embodiments, the implant is a prosthesis. According to particular embodiments, the implant is a joint prosthesis. According to particular embodiments, the implant is a hip-prosthesis and the biological sample is hip joint synovial fluid. According to other particular embodiments, the implant is a knee-prosthesis and the biological sample is preferably knee-joint synovial fluid.

In one embodiment according to the present invention, the at least one polypeptide to be detected is S100A9. In one embodiment according to the present invention, the at least one polypeptide to be detected is calprotectin. In one embodiment according to the present invention, the at least one polypeptide to be detected is S100A8.

In one embodiment according to the present invention, the level of the at least one polypeptide is detected by an assay suitable for detecting the at least one polypeptide in a synovial fluid sample, preferably the assay is a lateral flow immunochromatographic assay or an ELISA assay, more preferably an ELISA assay.

In one embodiment according to the present invention, the level of the at least one polypeptide is detected by an ELISA assay, the ELISA assay comprising the following steps: introducing the biological sample to a solid support coated with monoclonal antibodies specific for calprotectin, S100A8 or S100A9; removing the part of the biological sample that is not bound to the monoclonal antibodies from the solid support; introducing an enzyme conjugate to the solid support, the enzyme conjugate comprising enzyme-labelled polyclonal antibodies specific for calprotectin, S100A8 or S100A9, the enzyme preferably being alkaline phosphatase; removing the part of the enzyme conjugate that is not bound to the calprotectin, S100A8 or S100A9; introducing an enzyme substrate to the solid support; the enzyme substrate comprising a substrate to the enzyme conjugate, the enzyme substrate preferably being p-nitrophenyl phosphate; and measuring the amount of enzyme substrate that has been subjected to enzymatic treatment by the enzyme conjugate at a predetermined amount of time after the introduction of the enzyme substrate to the solid support; the solid support preferably being a microtiter plate.

In one embodiment according to the present invention, the diagnosis is solely based on the detected level of the at least one polypeptide.

In one embodiment according to the present invention, at least two biological samples are being provided, the two biological samples originating from different subjects; said subjects having an implant; with the proviso that at least one of said subjects suffers from pathology initiation. The level of at least one polypeptide selected from the group consisting of calprotectin, S100A8 and S100A9 are being detected in the biological samples; the biological samples being synovial fluid.

In one embodiment according to the present invention, the method further comprises grouping and stratifying the subject according to the diagnosis, identifying progressors and non-progressors, guiding treatment options, and identifying treatment response.

Use of a Kit

The present invention provides in a second aspect use of a kit for diagnosing implant related risk of revision in a subject with an implant, the kit being suitable for detecting a level of at least one polypeptide selected from the group consisting of calprotectin, S100A8 and S100A9 in a biological sample; wherein the biological sample is synovial fluid, the synovial fluid preferably being collected from the site of the implant.

In a preferred embodiment, the second aspect of the invention relates to the use of a kit for diagnosing implant related risk of revision in a subject with an implant in accordance with the method of the first aspect of the present invention.

In one embodiment according to the second aspect of the invention, the kit is a kit for conducting an ELISA assay or a kit for conducting a lateral flow immunochromatographic assay.

In a preferred embodiment according to the second aspect of the invention, the kit is a kit for conducting an ELISA assay.

In a preferred embodiment according to the second aspect of the invention, the kit is a kit for conducting an ELISA assay, the ELISA assay comprising the following steps: introducing a biological sample to a solid support coated with monoclonal antibodies specific for calprotectin, S100A8 or S100A9; removing the part of the biological sample that is not bound to the monoclonal antibodies from the solid support; introducing an enzyme conjugate to the solid support, the enzyme conjugate comprising enzyme-labelled polyclonal antibodies specific for calprotectin, S100A8 or S100A9: the enzyme preferably being alkaline phosphatase; removing the part of the enzyme conjugate that is not bound to the calprotectin, S100A8 or S100A9; introducing an enzyme substrate to the solid support; the enzyme substrate comprising a substrate to the enzyme conjugate, the enzyme substrate preferably being p-nitrophenyl phosphate; and measuring the amount of enzyme substrate that has been subjected to enzymatic treatment by the enzyme conjugate at a predetermined amount of time after the introduction of the enzyme substrate to the solid support; the solid support preferably being a microtiter plate.

In one embodiment according to the second aspect of the invention, the kit for conducting an ELISA assay comprises: a solid support coated with monoclonal antibodies specific for calprotectin, S100A8 or S100A9; at least one washing solution; an enzyme conjugate, the enzyme conjugate comprising enzyme-labelled polyclonal antibodies specific for calprotectin, S100A8 or S100A9, the enzyme preferably being alkaline phosphatase; and an enzyme substrate, the enzyme substrate comprising a substrate to the enzyme conjugate, the enzyme substrate preferably being p-nitrophenyl phosphate.

Composition for Use

The present invention provides in a third aspect a composition for use in the treatment of a subject that has been diagnosed with implant related risk of revision according to the method of claim 1, the composition comprising at least one agent selected from the group consisting of an anti-osteolytic agent, an anti-phlogistic/anti-inflammatory agent and any combination thereof.

In one embodiment according to the third aspect of the invention, the subject to be treated has been diagnosed with pathology initiation.

In another embodiment according to the third aspect of the invention, the composition comprises at least one agent which is suitable for treatment of a condition which is related to an undesirable high level of TNFα and/or undesirable high level of IL1β.

In another embodiment according to the third aspect of the invention, the composition comprises at least one agent selected from the group consisting of Bisphosphonates, Acetaminophens, NSAIDs, Diclofenac, Macrolides, Tetracyclines, Amphenicols, Cephalosporins, Sulfonamides, Trimethoprims, Lincosamides, Aminoglycosides, Quinolones, Tigracyclins, Vancomycin and Vancomycin-analogs, Gentamicin, Glucosamins, Chondroitins, Aspirin, Cortisone and any combination thereof.

In another embodiment according to the third aspect of the invention, the subject to be treated fails to show any noticeable symptoms with which implant related risk of revision is associated.

In another embodiment according to the third aspect of the invention, the subject to be treated is an asymptomatic subject.

In another embodiment according to the third aspect of the invention, the subject to be treated does not have any symptoms of implant related risk of revision.

In another embodiment according to the third aspect of the invention, the subject to be treated suffers from pathology initiation.

In another embodiment according to the third aspect of the invention implant related risk of revision is either acute pathology or pathology initiation; and the subject to be treated has not been diagnosed with acute pathology.

In another embodiment according to the third aspect of the invention the subject to be treated has been diagnosed with implant related risk of revision that is not caused by implant-associated infection. In one embodiment, implant-associated infection is selected from the group consisting of septic loosening, chronic joint infection, biofilm infection and/or any combination thereof.

In another embodiment according to the third aspect of the invention the subject to be treated has been diagnosed with implant related risk of revision that is not caused by metal-on-metal reaction.

DETAILED DESCRIPTION

Figure 1:
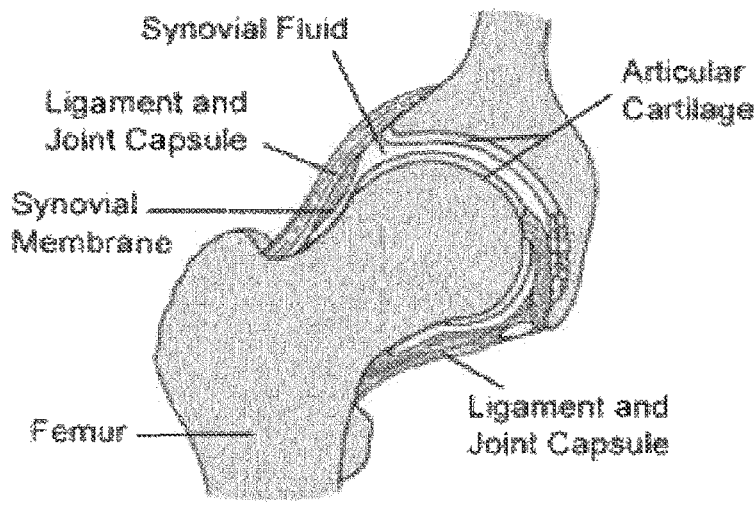
FIG. 1 illustrates a healthy hip joint.
Figure 2:
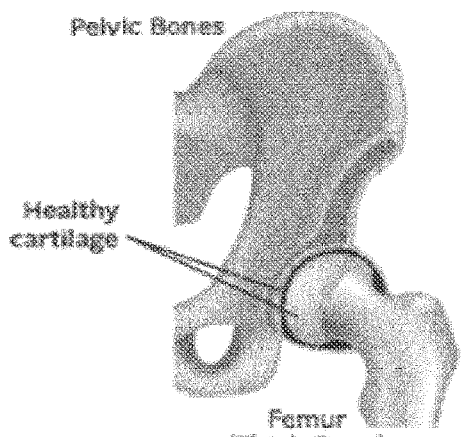
FIG. 2 illustrates a healthy hip joint as compared to a worn joint with exposed femoral bone which may be in direct contact with pelvic bone.
Figure 2:
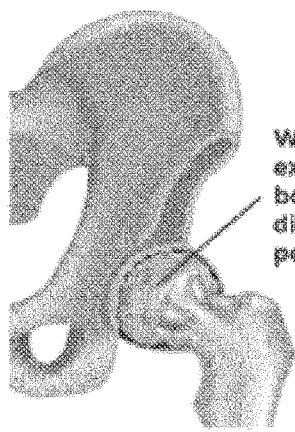
Figure 3:
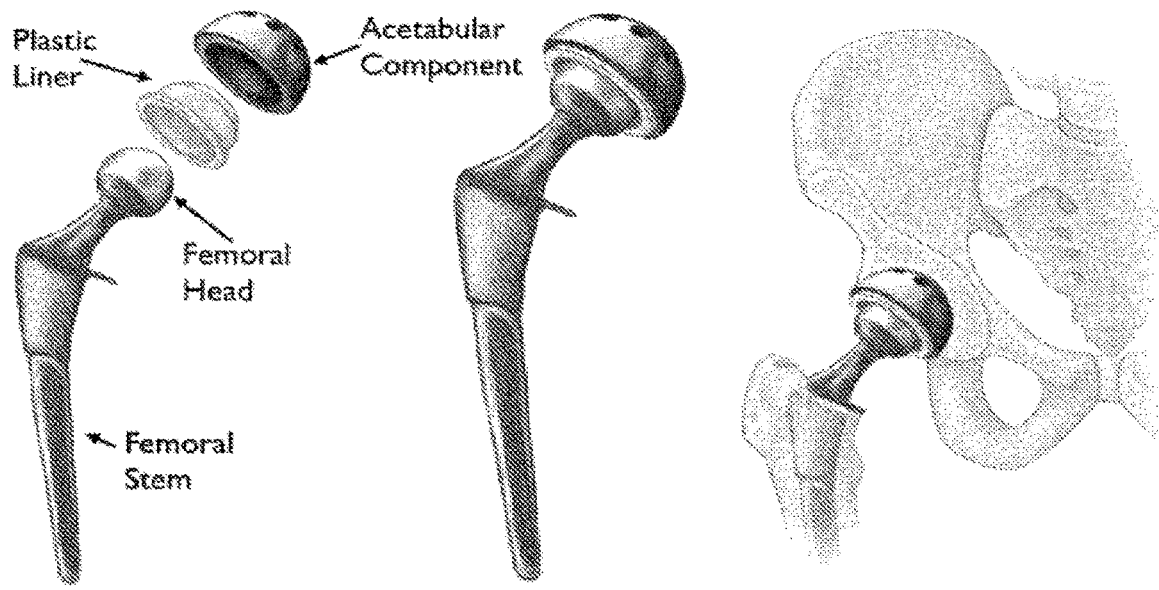
FIG. 3 illustrates a total hip replacement implant.

Unless specifically defined herein, all technical and scientific terms used have the same meaning as commonly understood by a skilled artisan in the fields of biochemistry and biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Where a numerical limit or range is stated herein, the endpoints are included. Also, all values and sub ranges within a numerical limit or range are specifically included as if explicitly written out.

Approximately 1.5 million total hip replacement (total hip arthroplasty—THA) operations are carried out world-wide annually. The expected failure rate of prosthetic implants over the first 10 years is approximately 3-5% and the failure rate is increasing for the next 10 years. Osteolysis and subsequent aseptic joint loosening, both belonging to the "pathology initiation" group, is the most common reason for joint revision. At an early stage, this condition is typically associated with micromovement at the implant-bone interface causing progressive destruction of bone. Initially, this condition is often painless and because of this symptomless interval the loss of bone stock may be massive before patients seek advice. By then, the conditions for a revision procedure may be unfavorable and the expected survival time for a new prosthesis is decreased. Thus, there is a need for methods which allows diagnosing early stage implant loosening even in asymptomatic patients.

Further, there is also a need for cost effective methods which allows identifying patients that is at risk of revision; i.e. separating the patients who is in the need of treatment from the patients with a stable implant that is in no need of treatment.

The present inventors have solved this need by having identified biomarkers, and in particular calprotectin, S100A8 and S100A9, which allow early stage diagnosis of implant loosening, even in asymptomatic patients.

Thus, a first aspect of the present invention relates to a method of diagnosing implant related risk of revision, the method comprising the following steps: providing a biological sample from a subject with an implant; detecting a level of at least one polypeptide selected from the group consisting of calprotectin, S100A8 and S100A9 in the biological sample; wherein the biological sample is synovial fluid, preferably synovial fluid from the site of the implant.

In one embodiment according to the present invention, the biological sample is synovial fluid collected at the site of the implant, e.g. an artificial joint synovial fluid.

In one embodiment according to the present invention, the implant is a joint implant. In another embodiment according to the present invention, the implant is a prosthesis such as a joint prosthesis and in particular a hip-prosthesis.

In one embodiment according to the present invention, the implant is a hip-prosthesis and the biological sample is hip joint synovial fluid.

Calprotectin belongs to the S100 family of proteins. The name derives from the fact that they are resistant to precipitation by ammonium sulfate, so that they are soluble even in 100 percent saturated (thus S100) ammonium sulfate solution. A common feature of these proteins is that they can bind calcium and zinc and thereby become resistant to enzymatic degradation; this is especially true for calprotectin.

Calprotectin is a complex of the mammalian proteins S100A8 and S100A9. Each of S100A8 and S100A9 contain two $Ca^{2+}$ binding sites, and calprotectin is able to bind a total of four calcium ions per dimer or eight calcium ions per tetramer. Calcium binding induces a conformational change in the complex that improves its affinity for transition metals, and promotes tetramer formation. A maximum of two transition metal ions may bind to each calprotectin S100A8-S100A9 dimer. This metal sequestration affords the complex antimicrobial properties.

According to particular embodiments, the at least one polypeptide to be detected is calprotectin. According to particular embodiments, the at least one polypeptide to be detected is S100A8. According to particular embodiments, the at least one polypeptide to be detected is S100A9.

A man skilled in the art will easily know how to detect calprotectin and its monomers in a biological sample. WO2013/132347, which is incorporated herein by reference in its entirety, discloses the use of an ELISA assay for determining the concentration of calprotectin in a biological sample. An alternative to the use of an ELISA assay is the well-known lateral flow immunochromatographic assay (LFA).

In one embodiment according to the present invention, the level of the at least one polypeptide is detected by an assay suitable for detecting the at least one polypeptide in a synovial fluid sample, preferably the assay is a lateral flow immunochromatographic assay or an ELISA assay, more preferably an ELISA assay.

In case of an ELISA assay, the assay preferably comprising the following steps: introducing the biological sample to a solid support coated with monoclonal antibodies specific for calprotectin, S100A8 or S100A9; removing the part of the biological sample that is not bound to the monoclonal antibodies from the solid support; introducing an enzyme conjugate to the solid support, the enzyme conjugate comprising enzyme-labelled polyclonal antibodies specific for calprotectin, S100A8 or S100A9, the enzyme preferably being alkaline phosphatase; removing the part of the enzyme conjugate that is not bound to the calprotectin, S100A8 or S100A9; introducing an enzyme substrate to the solid support; the enzyme substrate comprising a substrate to the enzyme conjugate, the enzyme substrate preferably being p-nitrophenyl phosphate; and measuring the amount of enzyme substrate that has been subjected to enzymatic treatment by the enzyme conjugate at a predetermined amount of time after the introduction of the enzyme substrate to the solid support; the solid support preferably being a microtiter plate.

Calprotectin comprises as much as 60% of the soluble protein content of the cytosol of a neutrophil. It is the amount of secreted calprotectin, S100A8 and/or S100A9 that is to be detected and not the intracellular content in intact cells present in the sample. Thus, it is essential that samples comprising cells are not subjected to treatment which would cause release of intracellular calprotectin, S100A8 and/or S100A9.

Thus, in one embodiment according to the present invention the at least one polypeptide to be detected represents calprotectin, S100A8 and/or S100A9 that has been secreted by cells. In another embodiment according to the present invention, the at least one polypeptide to be detected does not represent calprotectin, S100A8 and/or S100A9 that were part of the intracellular content of intact cells at the time of sampling.

In one embodiment according to the present invention, the diagnosis is solely based on the detected level of the at least one polypeptide.

As used herein, the term "subject" refers to an animal, and in particular a mammal such as a human. In one embodiment according to the present invention, the subject to be diagnosed is an asymptomatic subject, such as an asymptomatic animal and in particular an asymptomatic mammal such as an asymptomatic human. An asymptomatic human may e.g. be an asymptomatic patient.

In the context of the present invention, the term "implant" refers to a medical implant that is implanted in a living organism, such as humans. A medical implant is a man-made device, in contrast to a transplant, which is a transplanted biomedical tissue.

In one embodiment according to the present invention, the term "implant" refers to an orthopedic implant. An orthopedic implant is a medical device manufactured to replace a missing joint or bone or to support a damaged bone. The medical implant is typically fabricated using stainless steel and titanium alloys for strength and the plastic coating that is done on it acts as an artificial cartilage. Internal fixation is an operation in orthopedics that involves the surgical implementation of implants for the purpose of repairing a bone. Among the most common types of medical implants are the pins, rods, screws and plates used to anchor fractured bones while they heal.

In one preferred embodiment, the term "implant" refers to a medical device manufactured to replace a missing joint, such as a joint prosthesis and in particular a hip prosthesis.

In one embodiment according to the present invention a level <4 mg/l of the at least one polypeptide is indicative of a diagnosis of no implant related risk of revision, i.e. a stable implant. If a patient is diagnosed with no implant related risk of revision, the implant is stable and no further medical examination is necessary.

In the context of the present invention, any reference to a specific amount of the at least one polypeptide (e.g. less than 4 mg/L) refers to the specific amount as measured by the CALPROLAB™ Calprotectin ELISA (ALP) kit. The CALPROLAB™ Calprotectin ELISA (ALP) kit is further described in example 1. Said in other words, if a sample is said to contain 4 mg/L calprotectin, the sample contains 4 mg/L calprotectin as measured by the CALPROLAB™ Calprotectin ELISA (ALP) kit referred to in Example 1.

In another embodiment according to the present invention, a level >4 mg/L of the at least one polypeptide is indicative of a diagnosis of implant related risk of revision. The level of the at least one polypeptide referring to a level as measured by the CALPROLAB™ Calprotectin ELISA (ALP) kit referred to in Example 1. Patients suffering from implant related risk of revision have an increased risk of implant loosening and should be referred to a specialist for further medical examination.

A further medical examination may reveal whether the patient has an early stage loosening, i.e. pathology initiation, or acute pathology. While acute pathology requires revision surgery, patients having pathology initiation may benefit from drug therapy. If the drug therapy is not successful, revision surgery may be required at a later stage.

In the context of the present invention, the term "revision surgery" is intended to mean replacement of the implant, e.g. replacement of the prosthesis.

Figure 5:
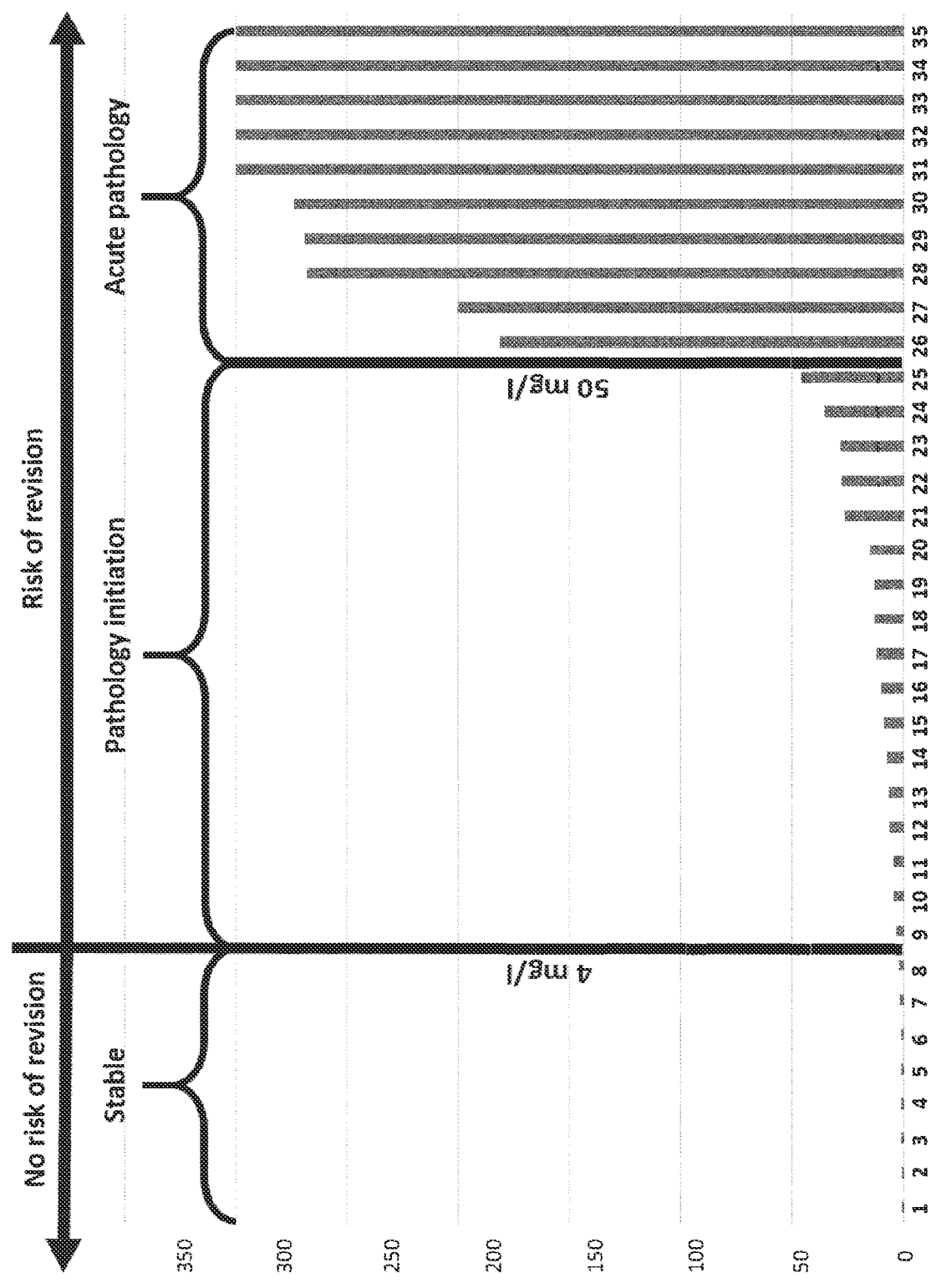
FIG. 5 illustrates the results of example 1 and provides an overview of the conditions that may be diagnosed by the method according to the present invention. The "no risk of revision" group representing patients with stable implants that is in no need of treatment. The "risk of revision" group representing patients with implants that is likely to need treatment. Further, the "risk of revision" group is divided in two subgroups. The group "pathology initiation" represents patients suffering from an early stage of loosening. This group may be subjected to drug-treatment and thereby increasing the chance of avoiding revision surgery. The group "acute pathology" represents patients suffering from late stage of loosening and is likely to be in immediate need of revision surgery. Each number on the X-axis refers to a sample from one patient. The numbers on the Y-axis refers to the amount of calprotectin (mg/L) in each sample.

Thus, in another embodiment according to the present invention a subject diagnosed with implant related risk of revision is a subject suffering from either pathology initiation or acute pathology (see FIG. 5).

Surprisingly, the inventors of the present invention have discovered that the results of the method of diagnosing implant related risk of revision may also indicate whether the patients suffering from implant related risk of revision suffers from early stage loosening, i.e. pathology initiation, or acute pathology.

Figure 4A:
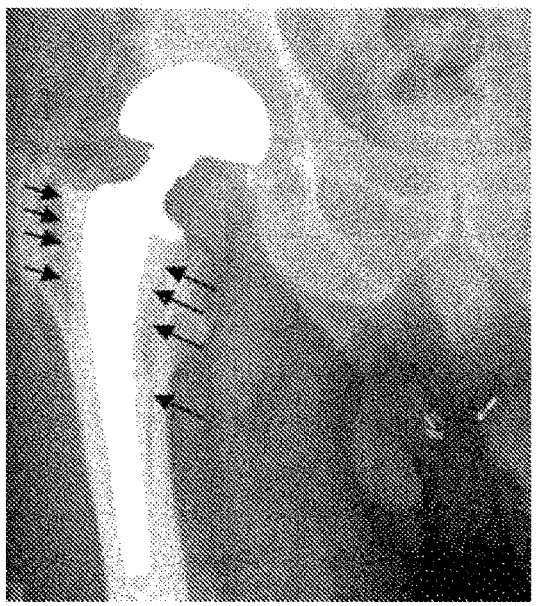
FIG. 4A illustrates a hip prosthesis displaying aseptic loosening (arrows).
Figure 4B:
FIG. 4B illustrates a dislocated hip prosthesis.

Thus, in another embodiment according to the present invention a level in the range 4-50 mg/L of the at least one polypeptide is indicative of pathology initiation. Pathology initiation refers to an early stage of prosthesis loosening which will require implant revision if left untreated. This condition is typically associated with micromovement at the implant-bone interface causing progressive destruction of bone. Initially, this condition is often painless and because of this symptomless interval the loss of bone stock may be massive before patients seek advice. Aseptic loosening (FIG. 4A), dislocation of implant (FIG. 4B), osteolysis and/or any combination thereof are examples of pathology initiation conditions.

Aseptic loosening is characterized by poorly vascularized connective tissue dominated by fibroblasts and macrophages. Subsequently, secretion of proinflammatory factors, gelatinases, and proteases contributes to periprosthetic osteolysis and to failure of the joint implant. Aseptic loosening can be the result of inadequate initial fixation, mechanical loss of fixation over time, or biologic loss of fixation caused by particle-induced osteolysis around the implant.

The term "osteolysis" generally refers to a problem common to artificial joint replacements such as total hip replacements, total knee replacements and total shoulder replacements. There are several biological mechanisms which may lead to osteolysis. In total hip replacement, the generally accepted explanation for osteolysis involves wear particles (worn off the contact surface of the artificial ball and socket joint). As the body attempts to clean up these wear particles (typically consisting of plastic or metal), it triggers an autoimmune reaction which causes resorption of living bone tissue. Osteolysis has been reported to occur as early as 12 months after implantation and is usually progressive.

The term "dislocation" generally refers to dislocation of the implant. Hip prosthesis dislocation mostly occur in the first 3 months after insertion, mainly because of incomplete scar formation and relaxed soft tissues. It takes eight to twelve weeks for the soft tissues injured or cut during surgery to heal. During this period, the hip ball can come out of the socket. The chance of this is diminished if less tissue is cut, if the tissue cut is repaired and if large diameter head balls are used. Dislocations occurring between 3 months and 5 years after insertion usually occur due to malposition of the components, or dysfunction of nearby muscles.

In one embodiment, pathology initiation is selected from the group consisting of inflammatory joint disease, osteoporosis, aseptic loosening, synovitis/synovial inflammation, wear and particle debris, misalignment of implant, fracture, ALVAL, stability of joint and/or implant including instability of one or both.

According to certain embodiments, inflammatory joint disease is selected from the group consisting of Adult-onset Still's disease, Ankylosing Spondylitis, Back Pain, Behcet's Disease, Bursitis, Calcium Pyrophosphate Deposition Disease (CPPD), Carpal Tunnel Syndrome, Chondromalacia Patella, Chronic Fatigue Syndrome, Complex Regional Pain Syndrome, Cryopyrin-Associated Periodic Syndromes (CAPS), Degenerative Disc Disease, Developmental-Dysplasia of Hip, Ehlers-Danlos, Familial Mediterranean Fever, Fibromyalgia, Fifth Disease, Giant Cell Arteritis, Gout, Hemochromatosis, Infectious Arthritis, Inflammatory Arthritis, Inflammatory Bowel Disease, Juvenile Arthritis, Juvenile Dermatomyositis (JD), Juvenile Idiopathic Arthritis (JIA), Juvenile Scleroderma, Kawasaki Disease, Lupus, Lyme Disease, Mixed Connective Tissue Disease, Myositis (inc. Polymyositis, Dermatomyositis), Osteoarthritis, Osteoporosis, Paget's, Palindromic Rheumatism, Patellofemoral Pain Syndrome, Pediatric Rheumatic Diseases, Pediatric SLE, Polymyalgia Rheumatica, Pseudogout, Psoriatic Arthritis, Raynaud's Phenomenon, Reactive Arthritis, Reflex Sympathetic Dystrophy, Reiter's Syndrome, Rheumatic Fever, Rheumatism, Rheumatoid Arthritis, Scleroderma, Sjögren's Disease, Spinal Stenosis, Spondyloarthritis, Systemic Juvenile Idiopathic Arthritis, Systemic Lupus Erythematosus, Systemic Lupus Erythematosus in Children & Teens, Systemic Sclerosis, Temporal Arteritis, Tendinitis, Vasculitis and Wegener's Granulomatosis.

In another embodiment according to the present invention a level in the range 4-50 mg/L, such as 5-50 mg/L, 10-50 mg/L, 20-50 mg/L or 30-50 mg/L, of the at least one polypeptide is indicative of pathology initiation. In another embodiment according to the present invention a level in the range 1-45 mg/L, 1-40 mg/L, 1-35 mg/L, 1-30 mg/L or 1-25 mg/L of the at least one polypeptide is indicative of pathology initiation.

In another embodiment according to the present invention, a level >50 mg/L of the at least one polypeptide is indicative of acute pathology. Acute pathology is typically a condition that in clinic is classified as implant-associated infection and/or metal-on-metal reaction. Patients suffering from acute pathology need immediate revision surgery.

The term "implant-associated infection" refers to a condition typically caused by bacteria that adhere to an implant surface and subsequently forms a biofilm at the implantation site. Formation of biofilm takes place in several stages, starting with rapid surface attachment, followed by multilayered bacterial cell proliferation and intercellular adhesion in an extracellular polysaccharide matrix.

The formation of biofilms on medical devices presents three major problems. First, bacterial communities on these surfaces represent a reservoir of bacteria that can be shed into the body, leading to a chronic infection. Second, biofilm bacteria are highly resistant to treatment with antibiotics; therefore, once these bacterial communities form, they are extremely difficult to eliminate with conventional antimicrobial therapies. Finally, because host responses and antimicrobial therapies are often unable to eliminate bacteria growing in a biofilm, a chronic inflammatory response at the site of the biofilm may be produced.

If bacterial adhesion occurs before tissue regeneration takes place, host defenses often cannot prevent surface colonization for certain bacterial species that are capable of forming a protective biofilm layer. Therefore, inhibiting bacterial adhesion is essential to prevent implant-associated infection, because biofilm are extremely resistant to both the immune system and antibiotics. Therefore, to succeed in orthopedic implants, implant materials must be habitable by bone-forming cells (favoring adhesion of osteoblasts), hinder formation of soft connective tissue (hindering adhesion of fibroblasts) and be anti-infective (discouraging bacterial adhesion).

In one embodiment according to the present invention, implant-associated infection is selected from the group consisting of septic loosening, chronic joint infection biofilm infection and/or any combination thereof.

The term "metal-on-metal reaction" typically refers to conditions relating to release of minute metallic particles or metal ions from wear of the implants, causing pain and disability. The cause of these failures remain controversial, and may include both design factors, technique factors, and factors related to patient immune responses (allergy type reactions).

In another embodiment according to the present invention a level >55 mg/L, such as >60 mg/L, >70 mg/L, >80 mg/L, >90 mg/L or >100 mg/L of the at least one polypeptide is indicative of acute pathology. In another embodiment according to the present invention, a level of the at least one polypeptide of 51-1000 mg/L, 55-1000 mg/L, 60-1000 mg/L, 70-1000 mg/L, 80-1000 mg/L, 90-1000 mg/L, 100-1000 mg/L, 51-900 mg/L, 51-850 mg/L, 51-800 mg/L, 51-700 mg/L, 51-650 mg/L, 51-600 mg/L, 51-550 mg/L or 51-500 mg/L is indicative of a diagnosis of acute pathology, such as a diagnosis of implant-associated infection.

The present invention provides a novel and easy way for separation of patients into two or more groups and subgroups thereof. A characterization into groups and subgroups is of interest as it can function as novel stratification of patients into therapy responder and no-responder groups as well as being used for increased diagnostic sensitivity and specificity.

Thus, in one embodiment according to the first aspect of the present invention, the method further comprises grouping and stratifying the subject according to its diagnosis, identifying progressors and non-progressors, guiding treatment options, and identifying treatment response.

In one embodiment according to the present invention, the method is for diagnosing pathology initiation.

In another embodiment according to the present invention, the method is not for diagnosing acute pathology.

In another embodiment according to the present invention, the method is for diagnosing implant related risk of revision that is not caused by implant-associated infection.

In another embodiment according to the present invention, the method is for diagnosing implant related risk of revision that is not caused by metal-on-metal reaction.

In another embodiment according to the present invention, the method further comprises a step of comparing the level of the at least one polypeptide in the biological sample with the level of the at least one polypeptide in a control sample. The control sample preferably being a synovial fluid sample from a subject not suffering from implant related risk of revision.

In another embodiment according to the present invention, at least two biological samples are being provided, the two biological samples originating from different subjects; said subjects having an implant; with the proviso that at least one of said subjects suffers from pathology initiation. A level of at least one polypeptide selected from the group consisting of calprotectin, S100A8 and S100A9 are being detected in the biological samples, the biological samples being synovial fluid.

A second aspect of the present invention relates to a kit for diagnosing implant related risk of revision in a subject with an implant, the kit being suitable for detecting a level of at least one polypeptide selected from the group consisting of calprotectin, S100A8 and S100A9 in a biological sample; wherein the biological sample is synovial fluid, the synovial fluid preferably being collected from the site of the implant.

In one embodiment according to the present invention, the kit is for diagnosing implant related risk of revision in a subject with an implant in accordance with the method according to the first aspect of the present invention.

In one embodiment according to the present invention, the kit is a kit for conducting an ELISA assay or a kit for conducting a lateral flow immunochromatographic assay.

In one embodiment according to the present invention, the kit is a kit for conducting an ELISA assay wherein the ELISA assay comprises the following steps: introducing a biological sample to a solid support coated with monoclonal antibodies specific for calprotectin, S100A8 or S100A9; removing the part of the biological sample that is not bound to the monoclonal antibodies from the solid support; introducing an enzyme conjugate to the solid support, the enzyme conjugate comprising enzyme-labelled polyclonal antibodies specific for calprotectin, S100A8 or S100A9; the enzyme preferably being alkaline phosphatase; removing the part of the enzyme conjugate that is not bound to the calprotectin, S100A8 or S100A9; introducing an enzyme substrate to the solid support; the enzyme substrate comprising a substrate to the enzyme conjugate, the enzyme substrate preferably being p-nitrophenyl phosphate; and measuring the amount of enzyme substrate that has been subjected to enzymatic treatment by the enzyme conjugate at a predetermined amount of time after the introduction of the enzyme substrate to the solid support; the solid support preferably being a microtiter plate.

In one embodiment according to the present invention, the kit is a kit for conducting an ELISA assay wherein the ELISA assay comprises: a solid support coated with monoclonal antibodies specific for calprotectin, S100A8 or S100A9; at least one washing solution; an enzyme conjugate, the enzyme conjugate comprising enzyme-labelled polyclonal antibodies specific for calprotectin, S100A8 or S100A9, the enzyme preferably being alkaline phosphatase; and an enzyme substrate, the enzyme substrate comprising a substrate to the enzyme conjugate, the enzyme substrate preferably being p-nitrophenyl phosphate.

In another embodiment according to the present invention, the kit is a kit for conducting an ELISA assay wherein the ELISA assay comprises the following steps: introducing a biological sample to a solid support coated with binding moieties, such as antibodies and in particular monoclonal antibodies, specific for calprotectin, S100A8 or S100A9; removing the part of the biological sample that is not bound to the binding moieties from the solid support; introducing an enzyme conjugate to the solid support, the enzyme conjugate comprising enzyme-labelled binding moieties, such as polyclonal antibodies, specific for calprotectin, S100A8 or S100A9; the enzyme preferably being alkaline phosphatase; removing the part of the enzyme conjugate that is not bound to the calprotectin, S100A8 or S100A9; introducing an enzyme substrate to the solid support; the enzyme substrate comprising a substrate to the enzyme conjugate, the enzyme substrate preferably being p-nitrophenyl phosphate; and measuring the amount of enzyme substrate that has been subjected to enzymatic treatment by the enzyme conjugate at a predetermined amount of time after the introduction of the enzyme substrate to the solid support; the solid support preferably being a microtiter plate.

In another embodiment according to the present invention, the kit is a kit for conducting an ELISA assay wherein the ELISA assay comprises the following steps: introducing a biological sample to a solid support coated with binding moieties (the binding moieties preferably being unlabeled), such as antibodies and in particular monoclonal antibodies, specific for calprotectin, S100A8 or S100A9; removing the part of the biological sample that is not bound to the binding moieties from the solid support; introducing labelled binding moieties specific for calprotectin, S100A8 or S100A9, the labelled binding moieties being able to produce a detectable signal proportional to the concentration of the at least one polypeptide to be detected; removing the part of the labelled binding moieties that are not bound to the calprotectin, S100A8 or S100A9; measuring the detectable signal to determine the level of the at least one polypeptide to be detected in the biological sample.

In one preferred embodiment, the binding moieties that are preferably unlabeled are monoclonal antibodies and the labeled binding moieties are polyclonal antibodies.

Suitable solid supports are well known in the art. However, one particularly suitable support is MaxiSorp™, produced by Nunc A/S, and described in U.S. Pat. No. 4,980,299 to Batz et al., employing synthetic resins such as polystyrene, Luran, polypropylene, or polyvinyl chloride. Various formats are known in the art for such solid supports; one particularly suitable format is the use of a microwell plate with 96 wells. Additional solid supports are described, for example, in D. Wild & W. Kusnezow, "Separation Systems" in The Immunoassay Handbook (D. Wild, ed., 3rd ed., Elsevier, Amsterdam, 2005), ch. 10, pp. 179-185, incorporated herein by this reference.

Coating of the solid support with the binding moieties is typically performed by methods known in the art. A particularly preferred buffer for coating the solid support with unlabeled monoclonal anti-S100A9 antibody is 0.1 M sodium citrate, pH 6.0. Typically, for coating a solid support, the monoclonal antibody is used at a concentration of from about 1 to 4 pg/mL, preferably about 2 pg/mL, in the buffer, such as the citrate buffer described above. Preferably, the solid support is covered with vapor tight adhesive plastic and stored at a temperature from about 0° C. to about 8° C., preferably about 4° C., for an incubation period of from about 6 hours to several weeks. Preferably, the incubation period is about 2 to 3 days. Alternatively, the solid support can be stored at a temperature of from about 9° C. to about 37° C.

Before the performance of the ELISA sandwich immunoassay, the solid support is washed to remove excess unbound antibodies. Typically, the solid support is washed with a conventional washing buffer such as phosphate buffered saline. Typically, the solid support is washed three to four times before the performance of the assay.

As used herein the term "binding moiety" refers to a molecule, complex or aggregate, that binds specifically or selectively to a target molecule, cell, particle, tissue or aggregate. Thus, a calprotectin binding moiety refers to a molecule, complex or aggregate, that binds specifically or selectively to calprotectin. Similarly, a S100A8 binding moiety refers to a molecule, complex or aggregate, that binds specifically or selectively to S100A8 and a S100A9 binding moiety refers to a molecule, complex or aggregate, that binds specifically or selectively to S100A9.

As used herein, the term "specific binding" refers to the specific recognition of one molecule as compared to substantially less recognition of other molecules. Specific binding examples include, but are not limited to, antibody-antigen interactions, enzyme-substrate interactions, and the like. In some embodiments, a binding moiety may have an intrinsic equilibrium association constant (KA) for the target no lower than about 105 $M^{-1}$ under ambient conditions such as a pH of about 6 to about 8 and temperature ranging from about 0° C. to about 37° C.

In one embodiment, the binding moieties are antibodies, antibody fragments, bispecific or other multivalent antibodies, or other antibody-based molecules or compounds. However, other binding moieties known in the art, such as aptamers, avimers or targeting peptides, may also be used.

As used herein, the term "antibody" refers to an immunoglobulin that specifically binds to and is thereby defined as complementary with a particular organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

The present invention provides a novel and easy way for separation of patients into two or more groups and subgroups thereof. A characterization into groups and subgroups is of interest as it can function as novel stratification of patients into therapy responder and no-responder groups.

Thus, a third aspect of the present invention relates to a composition for use in the treatment of a subject that has been diagnosed with implant related risk of revision according to the method of claim 1, the composition comprising at least one agent selected from the group consisting of an anti-osteolytic agent, an anti-phlogistic/anti-inflammatory agent and any combination thereof.

In one embodiment according to the third aspect of the present invention, the subject to be treated has been diagnosed with pathology initiation, preferably according to the method of the first aspect of the present invention.

In one embodiment according to the third aspect of the present invention, the composition comprises at least one agent which is suitable for treatment of a condition which is related to an undesirable high level of TNFα and/or undesirable high level of IL1β.

In one embodiment according to the third aspect of the present invention, the composition comprises at least one agent selected from the group consisting of Bisphosphonates, Acetaminophens, NSAIDs, Diclofenac, Macrolides, Tetracyclines, Amphenicols, Cephalosporins, Sulfonamides, Trimethoprims, Lincosamides, Aminoglycosides, Quinolones, Tigracyclins, Vancomycin and Vancomycin-analogs, Gentamicin, Glucosamins, Chondroitins, Aspirin, Cortisone and any combination thereof.

In one embodiment according to the third aspect of the present invention, the subject to be treated is an asymptomatic subject. In another embodiment, the subject to be treated does not have any symptoms of implant related risk of revision. In another embodiment, the subject to be treated suffers from pathology initiation.

In one embodiment according to the third aspect of the present invention, implant related risk of revision is either acute pathology or pathology initiation; and the subject to be treated preferably has not previously been diagnosed with acute pathology.

In one embodiment according to the third aspect of the present invention, the subject to be treated has been diagnosed with "implant related risk of revision that is not caused by implant-associated infection". Implant-associated infection is preferably selected from the group consisting of septic loosening, chronic joint infection, biofilm infection and/or any combination thereof.

In one embodiment according to the third aspect of the present invention, the subject to be treated has been diagnosed with "implant related risk of revision that is not caused by metal-on-metal reaction".

The invention will be described further in detail, with reference to the following example.

EXAMPLES

Example 1—KIT for Measuring Levels of Calprotectin in a Sample

The CALPROLAB™ Calprotectin ELISA (ALP) is a quantitative assay for measuring Calprotectin in samples. The assay is commercially available.
Principle of the Test:
In the ELISA, samples and standards are incubated in separate microtiter wells coated with monoclonal antibodies which bind the Calprotectin. After incubation and washing of the wells, bound Calprotectin is allowed to react with enzyme-labelled, immunoaffinity-purified Calprotectin-specific antibodies. After this reaction, the amount of enzyme bound in the microtiter wells is proportional to the amount of Calprotectin in the sample or standard, which is determined by incubation with a substrate for the enzyme giving a colored product. The color intensity is determined by absorbance using an ELISA plate reader, and is proportional with the concentration of Calprotectin in the standards and samples. The assay is calibrated using Calprotectin purified from leukocyte extract.
Reagents Supplied with the Kit:
Coated microtiter plate (MTP): 12 strips, 8 wells per strip, coated with affinity-purified monoclonal mouse antibodies specific for Calprotectin. The plate is stored in a sealed bag with desiccant.
Sample Dilution Buffer (5× conc.) (DIL 5×) *: 1×20 mL, 5× concentrate, to be diluted with distilled/deionized water; pH 8.0±0.2, yellow colored solution, bottle with blue cap. * Contains 0.1% Kathon and <0.1% sodium azide.
Washing Solution (20× conc.) (WASH BUF 20×) *: 1×50 mL, 20× concentrate, to be diluted with distilled/deionized water, for washing the microtiter wells; pH 7.8±0.2, clear solution, bottle with white cap. * Contains 0.1% Kathon.
Extraction Buffer (2.5× conc.) (EC EXTR BUF 2.5×) : 2×90 mL, 2.5× concentrate, to be diluted with distilled/deionized water; pH 8.0±0.2, clear solution, bottles with white caps.  Contains <0.1% sodium azide.
Calprotectin Standards (CAL A-F) ***: 6 vials with 1.0 mL, ready to use; yellow colored solution, vials with different colored caps: Standard A: Blue cap 0 ng/mL; Standard B: Green cap 7.8 ng/mL; Standard C: Yellow cap 31.3 ng/mL; Standard D: Red cap 62.5 ng/mL; Standard E: White cap 125 ng/mL; Standard F: Black cap 500 ng/mL.

Calprotectin Controls "Low" and "High" (CTR LOW; CTR HIGH)***: 2 vials with 1.0 mL, ready to use; yellow colored solution; Ctr Low: vial with brown cap; Ctr High: vial with purple cap.

Enzyme Conjugate (CONJ) **: 13 mL alkaline phosphatase-labelled, immunoaffinity-purified polyclonal rabbit antibodies against Calprotectin, ready to use; red colored solution, 25 mL Dynex reagent tube with white cap. ** Contains 0.02% methylisothiazolone and 0.02% bromonitrodioxane.

Enzyme Substrate Solution (pNPP) (SUB pNPP): 13 mL, ready to use; clear to faint yellow solution, opaque bottle with yellow cap. The bottle contains stabilizing pellets.

Note: If using a Dynex instrument, the substrate has to be transferred into a 25 mL Dynex reagent tube before running the test.

Synovial Samples from Patients with an Implant

Synovial samples were collected from 37 patients during revision surgery using a needle. Clinical diagnosis was decided by the surgeon based on his/her observation during revision surgery. The synovial samples were immediately frozen to a temperature of −20° C.

The samples were then thawed on ice. The thawed samples were then subjected to further preparation according to the procedure described below.

Reagent Preparation

All reagents, samples and controls are brought to room temperature before starting the test run.

The 2.5× Extraction buffer was diluted by adding 1 part (20 mL) to 1.5 parts (30 mL) distilled/deionized water in a clean vessel to a final volume of 50 mL, and mixed well.

The 5× concentrated Sample Dilution buffer was diluted by adding 1 part (20 mL) to 4 parts (80 mL) distilled/deionized water in a clean vessel to a final volume of 100 mL. The diluted sample diluent was mixed well.

The 20× concentrated washing solution was diluted by adding 1 part (10 mL) to 19 parts (190 ml) distilled/deionized water in a clean vessel to a final volume of 200 mL and mixed well.

The vials labelled with standard A-F, as well as the controls, contain 1.0 ml each of a ready to use solution. The concentration of Calprotectin is printed on the label of each vial. The highest standard (tube F) was omitted to produce a robust standard curve in the interesting calprotectin concentration range and to give room for an additional standard (50% dilution of standard tube C) in this range.

The enzyme conjugate tube contains 13 mL of alkaline phosphatase (ALP)-labelled, immunoaffinity-purified rabbit antibodies against Calprotectin in a buffer with 20 stabilizers, preservatives and an inert red dye. The solution is ready to use.

The enzyme substrate solution bottle contains 13 mL of p-nitrophenylphosphate solution. The solution is ready to use.

Measuring Levels of Calprotectin in Synovial Samples from Patients with an Implant 1) Synovial samples were first diluted 1:100 in 1× Extraction Buffer and mixed well by vortexing. Subsequently the samples were subjected to an additional 1:10 dilution in Sample Dilution Buffer, and mixed well by vortexing, generating a final dilution factor of 1:1000.

2) 100 µL of each standard, control and diluted synovial sample were added in the appropriate microplate wells. The standards were added in parallels of four, and the samples were added in triplicates.

3) The plate was covered with a sealing foil and incubated at room temperature for 40 minutes on a horizontal plate shaker at 600 rpm.

4) At the end of the incubation time, the liquid was removed, and the wells washed by adding 300 µL washing solution to each well. This procedure was repeated until a total of three washings have been performed. After each washing step, the plate is inverted and tapped on absorbent material to remove any remaining washing solution. Care is taken in the last of the three washing steps to remove any excess liquid.

5) 100 µL enzyme conjugate solution is added to each well.

6) The plate is covered with sealing foil and incubated at room temperature for 40 minutes on a horizontal plate shaker at 600 rpm.

7) The washing steps as described in item 4) is repeated. Three times with 300 µL washing solution per well.

8) 100 µL enzyme substrate solution is added to each well.

9) The plate is incubated at room temperature (without shaking) for 25 minutes, protected from light.

10) The optical density (OD) values at 405 nm is read using an ELISA reader.

11) A standard curve is prepared based on the optical measurements of the calprotectin standards and the known concentration of calprotectin in each standard sample.

12) Concentration of calprotectin in synovial samples are calculated based on the standard curve prepared in item 11).

Results "Implant Related Risk of Revision" (Table 1) 37 samples from patients with an implant were analyzed with respect to CRP and calprotectin. The results are presented in table 1. "Clinical diagnosis" refers to the correct clinical diagnosis. A test-diagnosis is set based on detected levels of calprotectin in synovial samples from the patients. If the calprotectin level is ≥4 mg/l, the patient has implant related risk of revision. However, if the calprotectin level is <4 mg/l, the patient has no implant related risk of revision. "Test (4 mg/L)" indicates whether the test-diagnosis provides a correct result as compared to the actual clinical diagnosis. TN (True Negative) refers to a situation where both the test- and the clinical diagnosis concludes that the patient has no risk of implant related risk of revision (diagnostic test provides a correct result). TP (True Positive) refers to a situation where both the test- and the clinical diagnosis concludes that the patient has risk of implant related risk of revision (diagnostic test provides a correct result). FN refers to a situation where the test diagnosis incorrectly concludes that the patient has no risk of implant related risk of revision (diagnostic test provides an incorrect result). FP refers to a situation where the test diagnosis incorrectly concludes that the patient has risk of implant related risk of revision (diagnostic test provides an incorrect result). Aseptic loosening, Dislocation, Septic loosening and Metal on metal are all associated with risk of implant related risk of revision. True positive and true negative results are presented in FIG. 5.

TABLE 1

| Sample# | CRP (mg/L)* | Clinical diagnosis | Calprotectin (mg/L) | Test (4 mg/L) |
|---|---|---|---|---|
| 1 | 0.5 | No risk of revision | 0.74 | TN |
| 2 | 2.0 | No risk of revision | 0.75 | TN |

TABLE 1-continued

| Sample# | CRP (mg/L)* | Clinical diagnosis | Calprotectin (mg/L) | Test (4 mg/L) |
|---|---|---|---|---|
| 3 | 11 | No risk of revision | 0.93 | TN |
| F1 | 39.0 | Aseptic loosening | 0.95 | FN |
| 4 | 2 | No risk of revision | 0.98 | TN |
| 5 | 4.0 | No risk of revision | 1.19 | TN |
| 6 | 1 | No risk of revision | 1.29 | TN |
| 7 | — | No risk of revision | 1.32 | TN |
| 8 | <1 | No risk of revision | 1.73 | TN |
| 9 | 4 | No risk of revision | 3.23 | TN |
| 10 | 1 | Aseptic loosening | 4.28 | TP |
| 11 | 0.5 | Aseptic loosening | 4.53 | TP |
| 12 | 3.0 | Dislocation | 6.05 | TP |
| 13 | 2 | Dislocation | 6.65 | TP |
| 14 | 2.0 | Dislocation | 7.44 | TP |
| 15 | 1 | Aseptic loosening | 8.82 | TP |
| 16 | 3.0 | Septic loosening | 9.88 | TP |
| 17 | <1 | Aseptic loosening | 12.3 | TP |
| 18 | 2.0 | Aseptic loosening | 12.75 | TP |
| 19 | 9 | Aseptic loosening | 12.91 | TP |
| 20 | 2 | Aseptic loosening | 15.27 | TP |
| 21 | — | Aseptic loosening | 26.36 | TP |
| 22 | 7.0 | Septic loosening | 27.72 | TP |
| 23 | — | Aseptic loosening | 28.11 | TP |
| 24 | 2.0 | Aseptic loosening | 35.39 | TP |
| 25 | 5 | Aseptic loosening | 46.16 | TP |
| F2 | 8 | No risk of revision | 105 | FP |
| 26 | 8.0 | Septic loosening | 181 | TP |
| 27 | 78.0 | Septic loosening | 181 | TP |
| 28 | 0.5 | Metal on metal | 250 | TP |
| 29 | 4 | Aseptic loosening | 268 | TP |
| 30 | 13 | Aseptic loosening | 269 | TP |
| 31 | 9 | Aseptic loosening | 274 | TP |
| 32 | 10.0 | Aseptic loosening | 300 | TP |
| 33 | — | Metal on metal | 300 | TP |
| 34 | 10 | Aseptic loosening | 300 | TP |
| 35 | 17 | Metal on metal | 300 | TP |

*C-reactive protein (CRP) is an annular (ring-shaped), pentameric protein found in blood plasma, whose levels rise in response to inflammation. It is an acute-phase protein of hepatic origin that increases following interleukin-6 secretion by macrophages and T cells. CRP is used mainly as a marker of inflammation. Measuring and charting CRP values can prove useful in determining disease progress or the effectiveness of treatments.

Total number of True Positive patients: 26
Total number of False Positive patients: 1
Total number of False Negative patients: 1
Total number of True Negative patients: 9
Sensitivity:
(Total number of True Positive patients)/(Total number of False Negative patients+Total number of True Positive patients)

Sensitivity=26/(1+26)=0.963

Specificity:
(Total number of True Negative patients)/(Total number of False Positive patients+Total number of True Negative patients)

Specificity=9/(1+9)=0.9

Negative Predictive Value:
(Total number of True Negative patients)/(Total number of False Negative patients+Total number of True Negative patients)

Negative Predictive Value=9/(1+9)=0.9

Positive Predictive Value
(Total number of True Positive patients)/(Total number of False Positive patients+Total number of True Positive patients)

Positive Predictive Value=26/(1+26)=0.963

Fisher Ex test provides a p-value of less than 0.0001 ($\alpha$=0.05).

Results "Pathology Initiation" (Table 2)

37 samples from patients with an implant were analyzed with respect to CRP and calprotectin. The results are presented in table 2. "Clinical diagnosis" refers to the correct clinical diagnosis. A test-diagnosis is set based on detected levels of calprotectin in synovial samples from the patients. If the calprotectin level is in the range 4-50 mg/l, the patient has indication of pathology initiation. "Test (4-50 mg/L)" indicates whether the test-diagnosis provides a correct result as compared to the correct clinical diagnosis. TN (True Negative) refers to a situation where both the test- and the clinical diagnosis concludes that the patient has no indication of pathology initiation. TP (True Positive) refers to a situation where both the test- and the clinical diagnosis concludes that the patient has indication of pathology initiation (diagnostic test provides a correct result). FN refers to a situation where the test diagnosis incorrectly concludes that the patient has no indication of pathology initiation (diagnostic test provides an incorrect result). FP refers to a situation where the test diagnosis incorrectly concludes that the patient has indication of pathology initiation (diagnostic test provides an incorrect result).

TABLE 2

| Sample# | CRP(mg/L)* | Clinical diagnosis | Calprotectin(mg/L) | Test (4-50 mg/L) |
|---|---|---|---|---|
| 1 | 0.5 | No indication of pathology initiation | 0.74 | TN |
| 2 | 2.0 | No indication of pathology initiation | 0.75 | TN |
| 3 | 11 | No indication of pathology initiation | 0.93 | TN |
| F1 | 39.0 | indication of pathology initiation | 0.95 | FN |
| 4 | 2 | No indication of pathology initiation | 0.98 | TN |
| 5 | 4.0 | No indication of pathology initiation | 1.19 | TN |
| 6 | 1 | No indication of pathology initiation | 1.29 | TN |
| 7 | — | No indication of pathology initiation | 1.32 | TN |
| 8 | <1 | No indication of pathology initiation | 1.73 | TN |
| 9 | 4 | No indication of pathology initiation | 3.23 | TN |
| 10 | 1 | indication of pathology initiation | 4.28 | TP |
| 11 | 0.5 | indication of pathology initiation | 4.53 | TP |
| 12 | 3.0 | indication of pathology initiation | 6.05 | TP |
| 13 | 2 | indication of pathology initiation | 6.65 | TP |
| 14 | 2.0 | indication of pathology initiation | 7.44 | TP |
| 15 | 1 | indication of pathology initiation | 8.82 | TP |
| 16 | 3.0 | Acute pathology | 9.88 | FP |
| 17 | <1 | indication of pathology initiation | 12.3 | TP |
| 18 | 2.0 | indication of pathology initiation | 12.75 | TP |

TABLE 2-continued

| Sample# | CRP(mg/L)* | Clinical diagnosis | Calprotectin(mg/L) | Test (4-50 mg/L) |
|---|---|---|---|---|
| 19 | 9 | indication of pathology initiation | 12.91 | TP |
| 20 | 2 | indication of pathology initiation | 15.27 | TP |
| 21 | — | indication of pathology initiation | 26.36 | TP |
| 22 | 7.0 | Acute pathology | 27.72 | FP |
| 23 | — | indication of pathology initiation | 28.11 | TP |
| 24 | 2.0 | indication of pathology initiation | 35.39 | TP |
| 25 | 5 | indication of pathology initiation | 46.16 | TP |
| F2 | 8 | No indication of pathology initiation | 105 | TN |
| 27 | 8.0 | Acute pathology | 181 | TN |
| 28 | 78.0 | Acute pathology | 181 | TN |
| 29 | 0.5 | Acute pathology | 250 | FN |
| 30 | 4 | indication of pathology initiation | 268 | FN |
| 31 | 13 | indication of pathology initiation | 269 | FN |
| 32 | 9 | indication of pathology initiation | 274 | FN |
| 33 | 10.0 | indication of pathology initiation | 300 | FN |
| 26 | — | Acute pathology | 300 | TN |
| 34 | 10 | indication of pathology initiation | 300 | FN |
| 35 | 17 | Acute pathology | 300 | TN |

*C-reactive protein (CRP) is an annular (ring-shaped), pentameric protein found in blood plasma, whose levels rise in response to inflammation. It is an acute-phase protein of hepatic origin that increases following interleukin-6 secretion by macrophages and T cells. CRP is used mainly as a marker of inflammation. Measuring and charting CRP values can prove useful in determining disease progress or the effectiveness of treatments.

Total number of True Positive patients: 14
Total number of False Positive patients: 2
Total number of False Negative patients: 6
Total number of True Negative patients: 15
Sensitivity:

(Total number of True Positive patients)/(Total number of False Negative patients+Total number of True Positive patients)

Sensitivity=14/(6+14)=0.7

Specificity:

(Total number of True Negative patients)/(Total number of False Positive patients+Total number of True Negative patients)

Specificity=15/(2+15)=0.882

Negative Predictive Value:

(Total number of True Negative patients)/(Total number of False Negative patients+Total number of True Negative patients)

Negative Predictive Value=15/(6+15)=0.714

Positive Predictive Value (Total number of True Positive patients)/(Total number of False Positive patients+Total number of True Positive patients)

Positive Predictive Value=14/(2+14)=0.875

Fisher exact test two tailed p value equal to 0.0001.

What is claimed is:

1. A method of treating a joint pathology, the method comprising:
   detecting a level of calprotectin of at least 4 mg/l in a biological sample from a human subject, wherein the biological sample is synovial fluid collected at the site of a joint; and
   administering to the human subject an anti-inflammatory drug therapy if the detected level of calprotectin is 4 mg/l to 50 mg/l, or administering joint surgery if the detected level of calprotectin is ≥50 mg/l;
   wherein the calprotectin in the biological sample is a secreted polypeptide and not an intracellular polypeptide of intact cells present in the biological sample.

2. The method of claim 1, wherein the biological sample is not subjected to treatment which would cause release of intracellular calprotectin into the biological sample.

3. The method of claim 1, wherein the joint is a hip joint and the biological sample is hip-joint synovial fluid.

4. The method of claim 1, wherein the joint is a knee joint and the biological sample is knee joint synovial fluid.

5. The method of claim 1, wherein the joint pathology is pathology initiation or acute pathology.

6. The method of claim 1, wherein the joint pathology is inflammatory joint disease, osteoporosis, synovitis, fracture, or osteolysis.

7. A method of treating a joint pathology in a subject, the method comprising:
   administering a therapy to a subject, wherein the subject has been identified as being at risk of a joint pathology by having a level of calprotectin of at least 4 mg/l in a synovial fluid sample collected from a site of a joint in the subject,
   wherein the therapy is an anti-inflammatory drug therapy if the detected level of calprotectin is 4 mg/l to 50 mg/l, or wherein the therapy is joint surgery if the detected level of calprotectin is ≥50 mg/l, and
   wherein the calprotectin in the biological sample is a secreted polypeptide and not an intracellular polypeptide of intact cells present in the biological sample.

8. The method of claim 7, wherein the joint is a hip joint and the biological sample is hip-joint synovial fluid.

9. The method of claim 7, wherein the joint is a knee joint and the biological sample is knee joint synovial fluid.

10. The method of claim 7, wherein the joint pathology is pathology initiation or acute pathology.

11. The method of claim 7, wherein the joint pathology is inflammatory joint disease, osteoporosis, synovitis, fracture, or osteolysis.

12. The method of claim 5, wherein the acute pathology comprises an implant-associated infection.

13. The method of claim 12, wherein the implant-associated infection is septic loosening, chronic joint infection, biofilm infection, or a combination thereof.

14. The method of claim 1, wherein the anti-inflammatory drug therapy comprises acetaminophen, NSAIDs, diclofenac, aspirin, cortisone, or a combination thereof.

15. The method of claim 1, further comprising administering to the human subject an anti-osteolytic drug therapy if the detected level of calprotectin is 4 mg/l to 50 mg/l.

16. The method of claim 15, wherein the anti-osteolytic drug therapy comprises bisphosphonates.

17. The method of claim 10, wherein the acute pathology comprises an implant-associated infection.

18. The method of claim 17, wherein the implant-associated infection is septic loosening, chronic joint infection, biofilm infection, or a combination thereof.

19. The method of claim 7, further comprising administering to the human subject an anti-osteolytic drug therapy if the detected level of calprotectin is 4 mg/l to 50 mg/l.

20. The method of claim 7, wherein the anti-inflammatory drug therapy comprises acetaminophen, NSAIDs, diclofenac, aspirin, cortisone, or a combination thereof.

* * * * *

UNITED STATES PATENT AND TRADEMARK OFFICE
CERTIFICATE OF CORRECTION

PATENT NO. : 12,146,885 B2
APPLICATION NO. : 18/067622
DATED : November 19, 2024
INVENTOR(S) : Stein Lian It is certified that error appears in the above-identified patent and that said Letters Patent is hereby corrected as shown below:

On the Title Page

Column 1, Line 1, Item (71) delete "Abcoude (NO)" and insert -- Abcoude (NL) --.

Column 2, Line 12-13, Item (56) delete "Journal ofInflammation," and insert -- Journal of Inflammation, --.

Column 2, Line 16, Item (56) delete "auto inflanunation:" and insert -- auto inflammation: --.

Column 2, Line 22, Item (56) delete ""Calprotectin (SIOOA8/A9) has" and insert -- "Calprotectin (S100A8/A9) has --.

Column 2, Line 43, Item (56) delete ""Alarmins SIO0A8/SIO0A9 aggravate" and insert -- "Alarmins S100A8/S100A9 aggravate --.

Column 2, Line 44, Item (56) delete "and predictosteophyte" and insert -- and predict osteophyte --.

Column 1, Page 2, Line 4, Item (56) delete "Protein, Hindawl" and insert -- Protein, Hindawi --.

Column 1, Page 2, Line 7, Item (56) delete "Van Der Vekiens" and insert -- Van Der Vekens --.

In the Specification

Column 4, Line 26, delete "is hip joint" and insert -- is hip-joint --.

Column 6, Line 23, delete "Tigracyclins, Vancomycin" and insert -- Tigecycline, Vancomycin --.

Column 6, Line 24, delete "Gentamicin, Glucosamins," and insert -- Gentamicin, Glucosamines, --.

Column 8, Line 3, delete "an artificial joint" and insert -- an artificial-joint --.

Signed and Sealed this
Fourth Day of February, 2025

Coke Morgan Stewart
*Acting Director of the United States Patent and Trademark Office*

Column 9, Line 63, delete "level >4" and insert -- level ≥4 --.

Column 15, Line 65, delete "Tigracyclins, Vancomycin" and insert -- Tigecycline, Vancomycin --.

Column 15, Line 66, delete "Gentamicin, Glucosamins," and insert -- Gentamicin, Glucosamines, --.

Column 17, Line 62, delete "an Implant" and insert -- an Implant. --.

Column 18, Line 32, delete "item 11)." and insert -- item 11. --.